(12) United States Patent
Choi et al.

(10) Patent No.: US 11,747,314 B2
(45) Date of Patent: Sep. 5, 2023

(54) GAS DETECTION INTELLIGENCE TRAINING SYSTEM AND OPERATING METHOD THEREOF

(71) Applicant: ELECTRONICS AND TELECOMMUNICATIONS RESEARCH INSTITUTE, Daejeon (KR)

(72) Inventors: Jae Hun Choi, Sejong-si (KR); Hwin Dol Park, Daejeon (KR); Chang-Geun Ahn, Sejong-si (KR); Do Hyeun Kim, Goyang-si (KR); Seunghwan Kim, Daejeon (KR); Hyung Wook Noh, Sejong-si (KR); YongWon Jang, Daejeon (KR); Kwang Hyo Chung, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 126 days.

(21) Appl. No.: 17/401,449

(22) Filed: Aug. 13, 2021

(65) Prior Publication Data

US 2022/0170900 A1    Jun. 2, 2022

(30) Foreign Application Priority Data

Dec. 2, 2020    (KR) .................. 10-2020-0166503

(51) Int. Cl.
*G01N 33/00* (2006.01)
*G06N 20/20* (2019.01)

(52) U.S. Cl.
CPC ..... *G01N 33/0062* (2013.01); *G01N 33/0075* (2013.01); *G06N 20/20* (2019.01); *G01N 2033/0068* (2013.01)

(58) Field of Classification Search
CPC ....... G01N 33/0062; G01N 2033/0068; G01N 33/0075; G01N 33/225; G06N 20/20; G06N 3/045; Y02A 90/10; Y02P 90/80
(Continued)

(56) References Cited

U.S. PATENT DOCUMENTS

| 10,803,382 B2 * | 10/2020 | Tayebi ..................... G06N 3/08 |
| 2009/0106820 A1 * | 4/2009 | Park ........................ G06F 21/32 |
| | | 726/2 |

(Continued)

FOREIGN PATENT DOCUMENTS

| CA | 2898740 C * | 9/2018 | ........ B01L 3/502761 |
| CA | 3053821 A1 * | 9/2018 | ............. G01F 1/661 |

(Continued)

OTHER PUBLICATIONS

D.-S. Lee et al., "Intelligent Olfactory Sensor", Electronics and Telecommunications Trends, vol. 34, No. 4, pp. 76-88, Aug. 1, 2019.
Lu Han et al., "A New Method of Mixed Gas Identification Based on a Convolutional Neural Network for Time Series Classification", Sensors (Basel)., pp. 1-23, Apr. 26, 2019.

*Primary Examiner* — Jeffrey P Aiello
(74) *Attorney, Agent, or Firm* — Rabin & Berdo, P.C.

(57) ABSTRACT

Disclosed are a gas detection intelligence training system and an operating method thereof. The gas detection intelligence training system includes a mixing gas measuring device that collects an environmental gas from a surrounding environment, generates a mixing gas based on the collected environmental gas and a target gas, senses the mixing gas by using a first sensor array and a second sensor array under a first sensing condition and a second sensing condition, respectively, and generates measurement data based on the sensed results of the first sensor array and the second sensor array, and a detection intelligence training (Continued)

device including a processor that generates an ensemble prediction model based on the measurement data.

16 Claims, 6 Drawing Sheets

(58) Field of Classification Search
USPC .................. 340/539.22; 700/28–30, 47–49; 702/1–3, 19–24, 179–182, 188–190; 703/2, 11; 706/12, 15, 45
See application file for complete search history.

(56) References Cited

U.S. PATENT DOCUMENTS

2018/0120277 A1\* 5/2018 Chang .................. G01N 33/007
2020/0271605 A1\* 8/2020 Carbonelli ............... G06N 3/04

FOREIGN PATENT DOCUMENTS

| CN | 109975501 A | \* | 7/2019 |
| JP | H06249810 A | | 9/1994 |
| JP | 2010112709 A | | 5/2010 |
| KR | 10-0917748 B1 | | 9/2009 |
| KR | 10-1720570 B1 | | 3/2017 |
| KR | 10-1972057 B1 | | 4/2019 |

\* cited by examiner

GAS DETECTION INTELLIGENCE TRAINING SYSTEM AND OPERATING METHOD THEREOF

CROSS-REFERENCE TO RELATED APPLICATIONS

This application claims priority under 35 U.S.C. § 119 to Korean Patent Application No. 10-2020-0166503 filed on Dec. 2, 2020, in the Korean Intellectual Property Office, the disclosures of which are incorporated by reference herein in their entireties.

BACKGROUND

Embodiments of the present disclosure described herein relate to a gas detection intelligence training system and an operating method thereof.

When someone smells something, gas particles included in the air chemically stimulate olfactory receptors in his/her nose. Accordingly, olfactory nerves are excited and then deliver a signal to an olfactory center in a temporal lobe of a brain. That is, it may be understood that smelling is physiologically identifying gas particles entering through a nose. Because gas particles that stimulate the olfactory receptors include properties of materials, the source of gas particles may be identified by detecting gas particles.

An olfactory sensor may measure the electrical resistance of a product resulting from a chemical reaction caused when gas particles are combined with a substance, such as a specific metal, may measure current or voltage by converting energy generated from the chemical reaction into electrical energy, or may measure a resonant frequency of a material changed by combining with a material. A material emitting gas particles may be identified based on aspects of these changes.

SUMMARY

Embodiments of the present disclosure provide a gas detection intelligence training system variously that mixes a gas obtained from surrounding environments with the target gas, senses the target gas from the mixed gas under various modalities and various sensing conditions, and trains a prediction model based on the sensed result, and an operating method thereof.

According to an embodiment, a gas detection intelligence training system includes a mixing gas measuring device that collects an environmental gas from a surrounding environment, generates a mixing gas based on the collected environmental gas and a target gas, senses the mixing gas by using a first sensor array and a second sensor array under a first sensing condition and a second sensing condition, respectively, and generates measurement data based on the sensed results of the first sensor array and the second sensor array, and a detection intelligence training device including a processor that generates an ensemble prediction model based on the measurement data.

According to an embodiment, an operating method of a gas detection intelligence training system includes generating a mixing gas from an environmental gas obtained from a surrounding environment and a target gas, under a plurality of sensing conditions, sensing the target gas from the mixing gas by using a first sensor array and a second sensor array, generating detection intelligence training data based on the sensed result, and generating an ensemble detection intelligence model based on the detection intelligence training data.

BRIEF DESCRIPTION OF THE FIGURES

The above and other objects and features of the present disclosure will become apparent by describing in detail embodiments thereof with reference to the accompanying drawings.

DETAILED DESCRIPTION

Hereinafter, embodiments of the present disclosure will be described in detail and clearly to such an extent that an ordinary one in the art easily implements the present disclosure.

Hereinafter, the best embodiment of the present disclosure will be described in detail with reference to accompanying drawings. With regard to the description of the present disclosure, to make the overall understanding easy, similar components will be marked by similar reference signs/numerals in drawings, and thus, additional description will be omitted to avoid redundancy.

Figure 1:
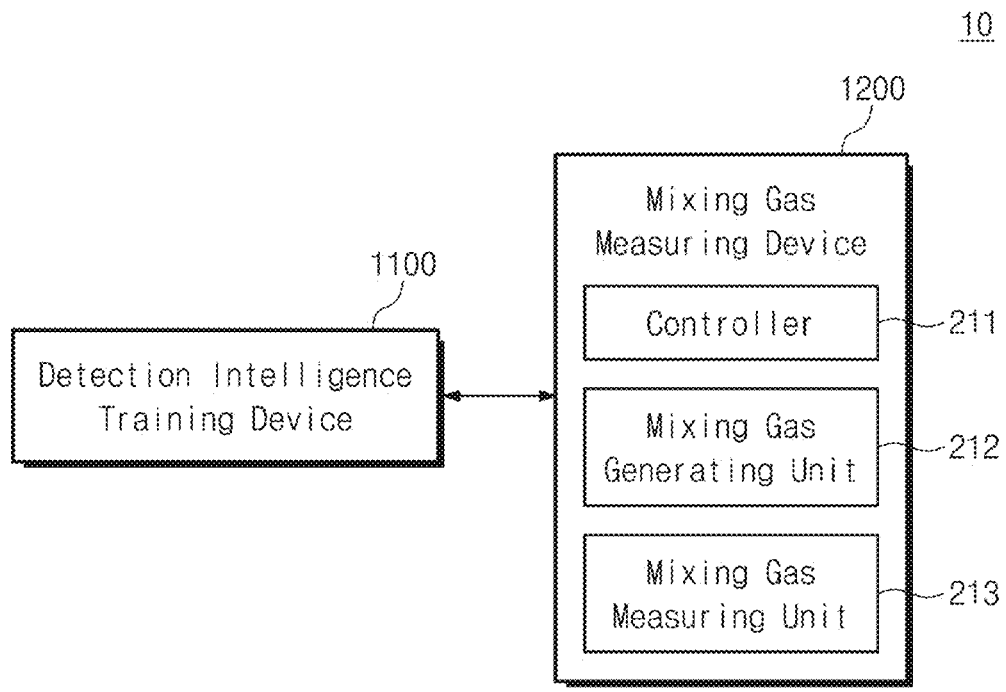
FIG. 1 is a block diagram of a gas detection intelligence training system, according to an embodiment of the present disclosure.

FIG. 1 is a block diagram of a gas detection intelligence training system 10, according to an embodiment of the present disclosure. Referring to FIG. 1, the gas detection intelligence training system 10 may include a detection intelligence training device 1100 and a mixing gas measuring device 1200.

The detection intelligence training device 1100 may sample measurement data generated by the mixing gas measuring device 1200. The detection intelligence training device 1100 may generate detection intelligence training data by preprocessing the sampled data. The detection intelligence training device 1100 may generate olfactory intelligence capable of detecting a target gas, by performing training based on the generated detection intelligence training data. The specific operation of the detection intelligence training device 1100 will be described later.

The mixing gas measuring device 1200 may collect an environmental gas from an external environment of the mixing gas measuring device 1200. The mixing gas measuring device 1200 may generate a mixing gas in which the environmental gas and the target gas are mixed in various ratios. The mixing gas measuring device 1200 may generate the measurement data by measuring the mixing gas by using sensor arrays and tagging, to a measured value, whether the target gas is included in the mixing gas. The mixing gas measuring device 1200 may include a controller 211, a mixing gas generating unit 212, and a mixing gas measuring unit 213. The mixing gas measuring device 1200 may further include a collector (not shown) for collecting gases and a gas storage device (not shown) for storing the collected gases. The specific operation of the mixing gas measuring device 1200 will be described later.

Figure 2:
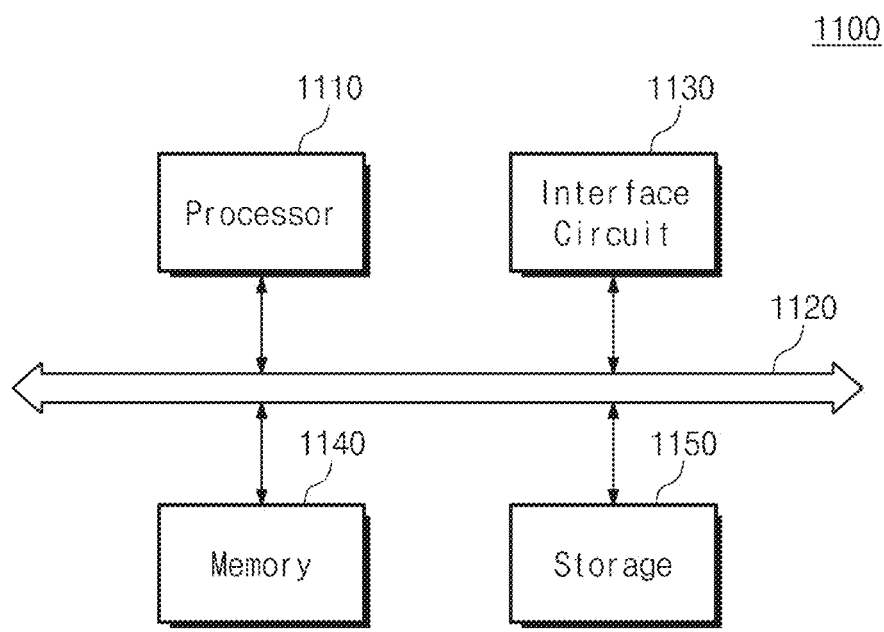
FIG. 2 is a block diagram of a detection intelligence training device of FIG. 1.

FIG. 2 is a block diagram of the detection intelligence training device 1100 of FIG. 1. Referring to FIGS. 1 and 2, the detection intelligence training device 1100 may include a processor 1110, a bus 1120, an interface circuit 1130, a memory 1140, and storage 1150.

The processor 1110 may perform a calculation for executing various software, firmware, or program codes loaded onto the memory 1140. The processor 1110 may perform a function as a central processing unit (CPU) of the detection intelligence training device 1100. The processor 1110 may also be referred to as a "digital signal processor (DSP)" or the like.

In some embodiments, the processor 1110 may generate a control signal for controlling the mixing gas measuring device 1200. For example, the processor 1110 may execute program codes for controlling the mixing gas measuring device 1200. The control signal generated by the processor 1110 may be provided to the controller 211 of the mixing gas measuring device 1200 through the interface circuit 1130. The controller 211 may control operations of the mixing gas generating unit 212 and the mixing gas measuring unit 213 in response to the received control signal.

The bus 1120 may provide a communication path between components of the detection intelligence training device 1100. The processor 1110, the interface circuit 1130, the memory 1140, and the storage 1150 may exchange data with each other through the bus 1120. The bus 1120 may be configured to support various communication formats used in the detection intelligence training device 1100.

Figure 6:
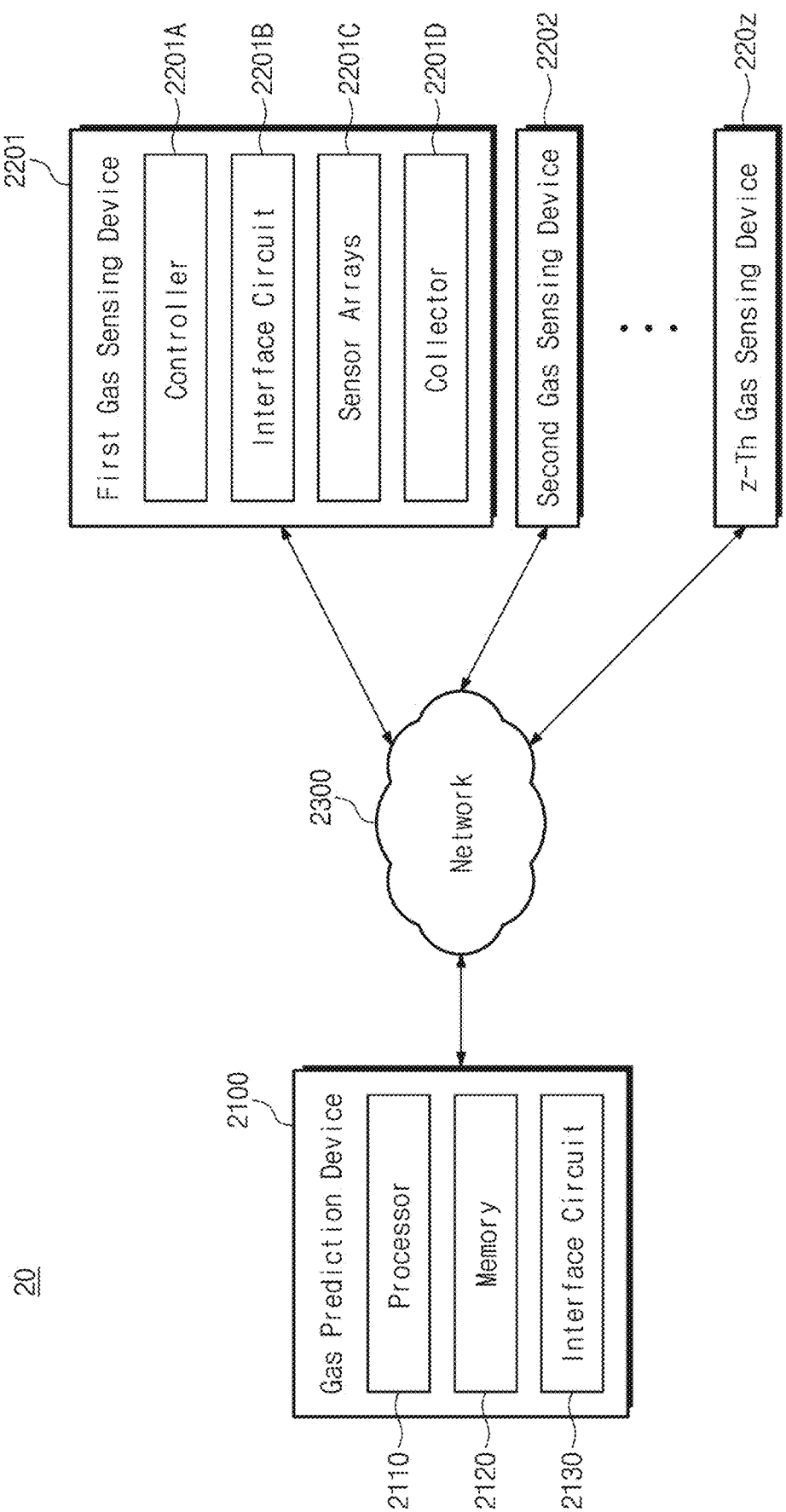
FIG. 6 is a block diagram of a gas detection system, according to an embodiment of the present disclosure.

The interface circuit 1130 may communicate with an external device (e.g., the mixing gas measuring device 1200 or a gas prediction device 2100 of FIG. 6) of the detection intelligence training device 1100. For example, the interface circuit 1130 may communicate with an external device of the detection intelligence training device 1100 based on various wired or wireless communication protocols. In some embodiments, the interface circuit 1130 may communicate with an external device of the detection intelligence training device 1100 through a wireless Internet such as Wifi or the like.

The interface circuit 1130 may further include a user interface for communicating with a user (not shown). For example, the interface circuit 1130 may provide the user with data generated by the processor 1110. In an embodiment, the user interface may include at least one of various output devices such as a monitor, a printer, or a lamp. The user interface may include at least one of various input devices such as a keyboard, a touchpad, a mouse, and a microphone.

The memory 1140 may store data and program codes, which is processed or to be processed by the processor 1110. The memory 1140 may function as a main memory device of the detection intelligence training device 1100. For example, i) programming codes, which is stored in the storage 1150 and which is used to generate training data from the measurement data generated by the mixing gas measuring device 1200, ii) programming codes, which is stored in the storage 1150 and which is used to train a detection intelligence model based on training data, and iii) data, which is stored in the storage 1150 and which is required to train the detection intelligence model may be loaded onto the memory 1140.

In an embodiment, the memory 1140 may include a dynamic random access memory (DRAM) or a static random access memory (SRAM). The memory 1140 may be referred to as a "buffer memory", "working memory", or "cache memory". Unlike the illustration of FIG. 2, the number of the memory 1140 may be one or more. The memory 1140 may be a non-transitory computer-readable medium storing codes executable by the processor 1110.

The storage 1150 may store data generated for long-term storage by the processor 1110, a file to be driven by the processor 1110, or various codes capable of being executed by the processor 1110. For example, the storage 1150 may store programming codes for generating training data executable by the processor 1110 and training detection intelligence model, and data generated as the programming codes for generating the training data and training the detection intelligence model is trained. The storage 1150 may function as an auxiliary memory device of the detection intelligence training device 1100. The storage 1150 may include a flash memory or the like. Unlike the illustration of FIG. 2, the storage 1150 may be implemented as an external device of the detection intelligence training device 1100.

Figure 3:
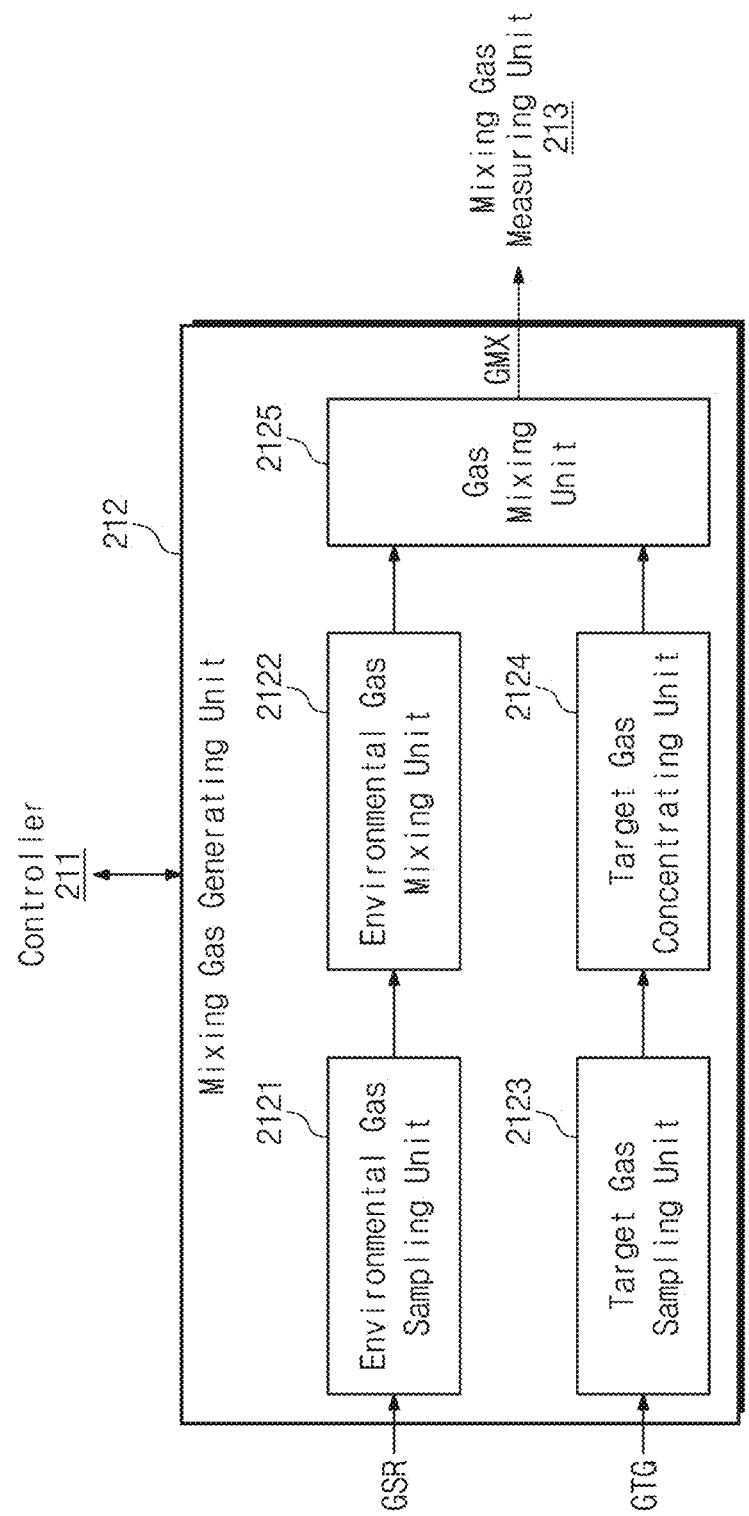
FIG. 3 is a block diagram of a mixing gas generating unit of a mixing gas measuring device of FIG. 1.

FIG. 3 is a block diagram of the mixing gas generating unit 212 of the mixing gas measuring device 1200 of FIG. 1. The mixing gas measuring device 1200 may collect gas in a specific space outside the mixing gas measuring device 1200. For example, the mixing gas measuring device 1200 may collect a gas, sample the collected gas, and generate a mixing gas GMX. The mixing gas GMX generated by the mixing gas measuring device 1200 may be used to generate training data for training the detection intelligence model of the detection intelligence training device 1100.

The controller 211 may control the mixing gas generating unit 212. For example, the controller 211 may generate a signal for controlling the mixing gas generating unit 212, by executing programming codes stored in storage (not shown) in the mixing gas measuring device 1200 or responding to a control signal received from an external device of the mixing gas measuring device 1200, such as the processor 1110.

The mixing gas generating unit 212 may include an environmental gas sampling unit 2121, an environmental gas mixing unit 2122, a target gas sampling unit 2123, a target gas concentrating unit 2124, and a gas mixing unit 2125.

An environmental gas GSR may be a gas collected from a specific space outside the mixing gas measuring device 1200. For example, the environmental gas GSR may be a gas collected from various types of spaces, for example, a container, such as a unit load device (ULD), a warehouse, an airplane, and an oral cavity of a human body.

The environmental gas sampling unit 2121 may sample the collected environmental gas GSR. The environmental gas sampling unit 2121 may classify the environmental gas GSR depending on a type. For example, the environmental gas sampling unit 2121 may classify the environmental gas GSR depending on the type of the environment in which the environmental gas GSR is collected.

The environmental gas sampling unit 2121 may pretreat the environmental gas GSR. For example, the environmental gas sampling unit 2121 may classify the classified the environmental gas GSR and may remove impurities from the environmental gas GSR. The environmental gas sampling unit 2121 may remove moisture or contaminants from the environmental gas GSR. The environmental gas sampling unit 2121 may deliver the pretreated environmental gas to the environmental gas mixing unit 2122.

The environmental gas mixing unit 2122 may combine sampled environmental gases. For example, under the control of the controller 211, the environmental gas mixing unit 2122 may control the opening of valves of devices that respectively store the sampled environmental gases. In an embodiment, when the number of types of sampled environmental gases is 'm', the environmental gas mixing unit 2122 may combine environmental gases in $_mC_{m-1}$ combinations. The environmental gas mixing unit 2122 may deliver the combined environmental gas to the gas mixing unit 2125.

The target gas sampling unit 2123 may sample a target gas GTG. The target gas sampling unit 2123 may deliver the sampled target gas to the mixing gas generating unit 212.

The target gas GTG may be the type of a gas to be detected (or trained) by using the detection intelligence training device 1100. For example, the target gas GTG may be a drug gas, a gas associated with a disease, a gas used for meat processing, or a respiratory gas, but is not limited thereto.

The target gas sampling unit 2123 may generate gases of various concentrations from the target gas GTG. For example, the target gas sampling unit 2123 may sample a specific kind of the target gas GTG at a concentration appropriate for operations of the mixing gas measuring unit 213 or the detection intelligence training device 1100. The target gas sampling unit 2123 may sample the target gas GTG at various concentrations such as parts per million (ppm), parts per billion (ppb), and parts per trillion (ppt).

The mixing gas generating unit 212 may generate the mixing gas GMX from gases thus sampled and pretreated. The mixing gas GMX may be a gas obtained by mixing the environmental gas GSR and the target gas GTG in various ratios. The concentration of the target gas GTG included in the mixing gas GMX may be adjusted by the controller 211.

The mixing gas generating unit 212 may tag the generated mixing gas GMX to the target gas GTG. The mixing gas generating unit 212 may deliver the mixing gas GMX to the detection intelligence training device 1100.

The target gas concentrating unit 2124 may adjust the concentration of the sampled target gas. For example, under the control of the controller 211, the target gas concentrating unit 2124 may control opening of valves of devices that respectively store the sampled target gases. The target gas concentrating unit 2124 may concentrate the target gas by controlling opening of the valves. The target gas concentrating unit 2124 may deliver the concentrated target gas to the gas mixing unit 2125.

The gas mixing unit 2125 may mix the combined environmental gas and the concentrated target gas. For example, with regard to one concentrated target gas, the gas mixing unit 2125 may control the opening of valves of devices respectively storing gases such that the combined environmental gases of all possible combinations are mixed. That is, with regard to one concentrated target gas, the gas mixing unit 2125 may generate $_mC_{m-1}$ types of mixing gases. The gas mixing unit 2125 may tag the generated mixing gas GMX to the corresponding target gas. The gas mixing unit 2125 may provide the mixing gas GMX to the mixing gas measuring unit 213.

Figure 4:
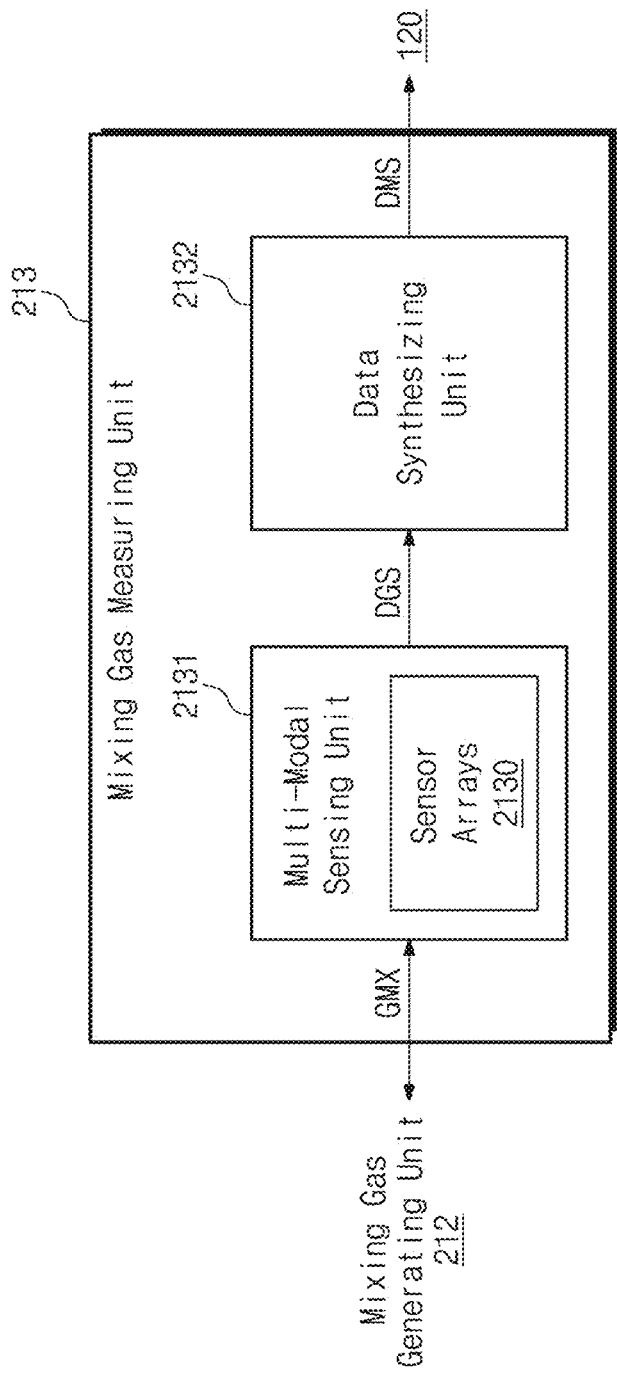
FIG. 4 is a block diagram of the mixing gas measuring unit of FIG. 1.

FIG. 4 is a block diagram of the mixing gas measuring unit 213 of FIG. 1. Referring to FIGS. 1 to 4, the mixing gas measuring unit 213 may include a multi-modal sensing unit 2131 and a data synthesizing unit 2132.

The multi-modal sensing unit 2131 may include sensor arrays 2130. The multi-modal sensing unit 2131 may adjust the sensing condition of each of the sensor arrays 2130.

The sensor arrays 2130 may be implemented as arrays including a plurality of olfactory sensors. For example, each of the sensor arrays 2130 may be implemented as an array of olfactory sensors such as metal oxide semiconductor (MOS) sensors, electrochemical sensors (ECSs), photoionization detector sensors, catalytic combustion sensors, polymer sensors, surface plasmon resonance (SPR) sensors, microcantilever sensors, and the like.

Each of the sensor arrays 2130 may have different modalities depending on an implementation method. For example, the first sensor array may have a first modality based on sensors included in a first sensor array.

For example, under the control of the controller 211, the multi-modal sensing unit 2131 may vary characteristics of an input signal, such as a waveform of a voltage, a current, or a control signal, which is applied to each of the sensors included in the sensor arrays 2130. Accordingly, the sensor arrays 2130 may provide sensing data associated with various modality and various sensing conditions.

Under the control of the controller 211, the multi-modal sensing unit 2131 may distribute the gas generated by the mixing gas generating unit 212 to the sensor arrays 2130. For example, the multi-modal sensing unit 2131 may distribute the mixing gas GMX to first to n-th sensor arrays included in the sensor arrays 2130. Herein, 'n' may be a natural number.

Under the control of the multi-modal sensing unit 2131, the sensor arrays 2130 may sense the mixing gas GMX under various conditions. The multi-modal sensing unit 2131 may generate multi-modal sensing data DMS from the sensed results of the sensor arrays 2130. The multi-modal sensing unit 2131 may transmit the multi-modal sensing data DMS to the data synthesizing unit 2132.

In some embodiments, each of the sensor arrays 2130 may sense the mixing gas GMX included in a chamber. In the chamber, the flow of the mixing gas GMX may be maintained uniformly. Accordingly, the accuracy of the sensor arrays 2130 may be improved.

The data synthesizing unit 2132 may synthesize the multi-modal sensing data DMS. For example, the data synthesizing unit 2132 may classify the multi-modal sensing data DMS based on the target gas GTG. The data synthesizing unit 2132 may synthesize the classified multi-modal sensing data DMS as time goes on, and may tag the synthesized result to the corresponding target gas GTG. The data synthesizing unit 2132 may provide a measurement data preprocessing unit 1210 with the synthesized data as measurement data DGS. The measurement data DGS may be time-series.

Figure 5:
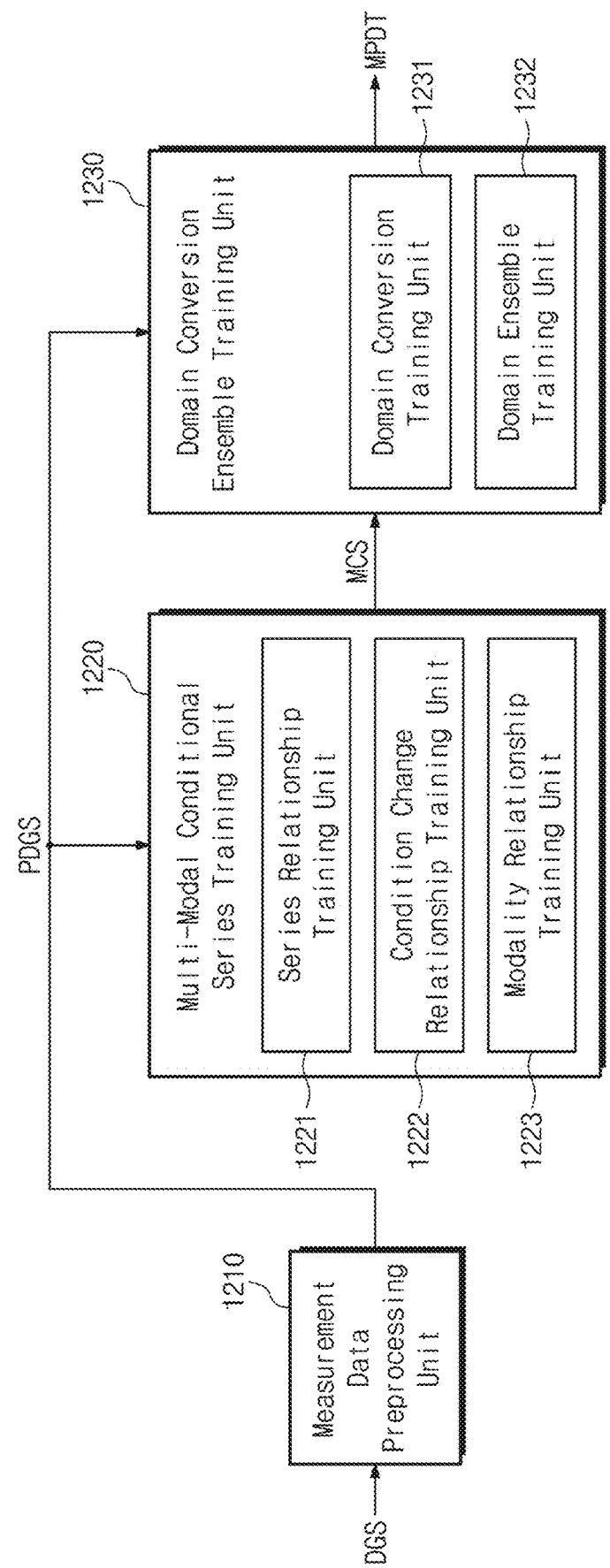
FIG. 5 is a block diagram of a detection intelligence training device, according to an embodiment of the present disclosure.

FIG. 5 is a block diagram of the detection intelligence training device 1100, according to an embodiment of the present disclosure. Referring to FIGS. 1 to 5, the detection intelligence training device 1100 may include the measurement data preprocessing unit 1210, a multi-modal conditional series training unit 1220, and a domain conversion ensemble training unit 1230.

In some embodiments, the processor 1110 of the detection intelligence training device 1100 may execute programming codes for executing the measurement data preprocessing unit 1210, the multi-modal conditional series training unit 1220, and the domain conversion ensemble training unit 1230. The programming codes for executing the measurement data preprocessing unit 1210, the multi-modal conditional series training unit 1220, and the domain conversion ensemble training unit 1230 may be stored in the storage 1150, and then may be loaded onto the memory 1140.

The measurement data preprocessing unit 1210 may receive the measurement data DGS from the mixing gas measuring unit 213. The measurement data preprocessing unit 1210 may preprocess the measurement data DGS. For example, the measurement data preprocessing unit 1210 may sample the measurement data DGS, may detect the abnormality of the measurement data DGS and then may compensate for the abnormality, may process a missing value of the measurement data DGS, or may normalize the measurement data DGS. The measurement data preprocessing unit 1210 may provide the preprocessed measurement data DGS as detection intelligence training data PDGS to the multi-modal conditional series training unit 1220 and the domain conversion ensemble training unit 1230.

The multi-modal conditional series training unit 1220 may include a series relationship training unit 1221, a condition change relationship training unit 1222, and a modality relationship training unit 1223. The series relationship training unit 1221, the condition change relationship training unit 1222, and the modality relationship training unit 1223 may perform various types of machine learning algorithms or deep learning algorithms, such as convolution neural network (CNN) or recurrent neural network (RNN).

The series relationship training unit 1221 may train the correlation between pieces of data, which have the same modality and the same sensing condition, from among the detection intelligence training data PDGS. For example, under the same modality and the same sensing condition, the series relationship training unit 1221 may divide sensing values, which are tagged to the type of the specific target gas GTG, into a plurality of different sample series for each time and then may list the divided results. In this case, the relationship between the type of the tagged target gas GTG and each of the sensor arrays 2130 may be expressed as a sensing value. The series relationship training unit 1221 may perform a supervised learning algorithm on the plurality of sample series by setting the target gas GTG tagged with the detection intelligence training data PDGS, to a label. In other words, the series relationship training unit 1221 may perform the supervised learning algorithm on each of the sample series by setting a time point, at which the target gas GTG is most accurately sensed for a sample, to attention.

The condition change relationship training unit 1222 may train the correlation between pieces of data, which have the same modality but are generated under different sensing conditions, from among the detection intelligence training data PDGS. For example, the condition change relationship training unit 1222 may perform a learning algorithm on the first to k-th sensing condition data sets, which are tagged to the type of the specific target gas GTG under the same modality, from among the detection intelligence training data PDGS. In other words, the condition change relationship training unit 1222 may perform training by setting a sensing condition that the target gas GTG is most accurately sensed, to attention.

The modality relationship training unit 1223 may train the correlation between pieces of data, which have different modality data, from among the detection intelligence training data PDGS. For example, the modality relationship training unit 1223 may perform a learning algorithm on the first to n-th modality data sets, which are tagged to the type of the target gas GTG under a specific sensing condition, from among the detection intelligence training data PDGS. In other words, the modality relationship training unit 1223 may perform training, by setting a modality at which the target gas GTG is most accurately sensed, from among the first to n-th modalities to attention.

The multi-modal conditional series training unit 1220 may deliver, to the domain conversion ensemble training unit 1230, a conditional detection intelligence model MCS generated through the series relationship training unit 1221, the condition change relationship training unit 1222, and the modality relationship training unit 1223. The multi-modal conditional series training unit 1220 may provide the conditional detection intelligence model MCS for each of the first to n-th modalities under a specific condition.

The domain conversion ensemble training unit 1230 may include a domain conversion training unit 1231 and a domain ensemble training unit 1232. The domain conversion ensemble training unit 1230 may receive the detection intelligence training data PDGS from the measurement data preprocessing unit 1210. The domain conversion ensemble training unit 1230 may receive the conditional detection intelligence model MCS from the multi-modal conditional series training unit 1220. The domain conversion ensemble training unit 1230 may select a target domain from among the first to n-th modalities. With regard to the selected target domain, the domain conversion ensemble training unit 1230 may generate an ensemble detection intelligence model MPDT based on the detection intelligence training data PDGS and the conditional detection intelligence model MCS. The domain conversion ensemble training unit 1230 may generate the ensemble detection intelligence model MPDT for each of the first to n-th modalities.

The domain conversion training unit 1231 may convert a training model (e.g. the conditional detection intelligence model MCS of a specific modality) in a specific domain into a training model in another domain. For example, the domain conversion training unit 1231 may train a domain conversion detection intelligence model for a specific sensing condition based on the data set in the target domain (i.e. of target modality) among the detection intelligence training data PDGS and the conditional detection intelligence model MCS. The domain conversion training unit 1231 may use various transfer learning algorithms. The domain conversion training unit 1231 may generate domain conversion detection intelligence models for each of the first to k-th sensing conditions with respect to the target domain.

For example, the domain conversion training unit 1231 may train a conditional detection intelligence model for the first modality and first sensing condition with the detection intelligence training data of the target domain. Accordingly, a domain conversion detection intelligence model for the first sensing condition of the target domain may be generated.

The domain ensemble training unit 1232 may generate the ensemble detection intelligence model MPDT for the target domain from the domain conversion detection intelligence models for the target domain. For example, the domain ensemble training unit 1232 may train the domain conversion detection intelligence models for each of the first to k-th sensing conditions of the target domain with data for the target domain among the detection intelligence training data PDGS. Accordingly, the ensemble detection intelligence model MPDT of the target domain may be generated by combining the domain conversion detection intelligence models for each of the first to k-th sensing conditions of the target domain. For example, the domain ensemble training unit 1232 may combine domain conversion detection intelligence models by using various methods such as voting, bagging, or boosting. The generated ensemble detection intelligence model MPDT may be stored in a database in the storage 1150.

FIG. 6 is a block diagram of a gas detection system 20, according to an embodiment of the present disclosure. Referring to FIGS. 1 to 6, the gas detection system 20 may include the gas prediction device 2100, first to z-th gas sensing devices 2201 to 220z, and a network 2300.

The gas prediction device 2100 may include a processor 2110, a memory 2120, and an interface circuit 2130. The processor 2110 may perform a calculation for executing various software, firmware, or program codes loaded onto the memory 2120. For example, the processor 2110 may execute programming codes, which is loaded onto the memory 2120 and which is used to detect the target gas GTG based on the ensemble detection intelligence model MPDT. The processor 2110 may perform a function as a central processing unit (CPU) of the gas prediction device 2100.

The memory 2120 may store data and program codes, which is processed or to be processed by the processor 2110. The memory 2120 may function as a main memory device of the gas prediction device 2100. For example, the ensemble detection intelligence model MPDT provided from the detection intelligence training device 1100 and multi-modal conditional measurement data received from the first to z-th gas sensing devices 2201 to 220z may be loaded onto the memory 2120. The memory 2120 may include a DRAM or an SRAM. The memory 2120 may be a non-transitory computer-readable medium storing codes executable by the processor 2110.

The programming codes, which are loaded onto the memory 2120 and then and executed by the processor 2110 and which is used to detect the target gas GTG based on the ensemble detection intelligence model MPDT, may include instructions for predicting whether a target gas is included in the gas collected by the first to z-th gas sensing devices 2201 to 220z. For example, the processor 2110 may predict whether the target gas is included in the gas collected by the first to z-th gas sensing devices 2201 to 220z, by using the ensemble detection intelligence model MPDT, which is generated by the detection intelligence training device 1100, and the multi-modal conditional measurement data received from the first to z-th gas sensing devices 2201 to 220z. The processor 2110 may provide the prediction result to a user or an external device such as the first to z-th gas sensing devices 2201 to 220z through the interface circuit 2130.

The processor 2110 may generate prediction data based on multi-modal conditional measurement data and the ensemble detection intelligence model MPDT. For example, the processor 2110 may preprocess multi-modal conditional measurement data. The processor 2110 may preprocess multi-modal conditional measurement data in a similar manner to that of the measurement data preprocessing unit 1210. The processor 2110 may predict a target gas type included in the preprocessed multi-modal conditional measurement data by using the ensemble detection intelligence model MPDT. The processor 2110 may provide the prediction result as prediction data to the interface circuit 2130.

The interface circuit 2130 may communicate with an external device of the gas prediction device 2100. For example, the interface circuit 2130 may communicate with the detection intelligence training device 1100 of the gas detection intelligence training system 10 and the network 2300 based on various wired or wireless communication protocols. In some embodiments, the interface circuit 2130 may communicate with the detection intelligence training device 1100 of the gas detection intelligence training system 10 and the network 2300 through a wireless Internet such as Wifi or the like.

The interface circuit 2130 may receive the ensemble detection intelligence model MPDT from the detection intelligence training device 1100. The interface circuit 2130 may receive multi-modal conditional measurement data from the first to z-th gas sensing devices 2201 to 220z through the network 2300. The interface circuit 2130 may store the received ensemble detection intelligence model MPDT and multi-modal conditional measurement data in storage (not shown) in the gas prediction device 2100.

The interface circuit 2130 may further include a user interface for communicating with a user (not shown). For example, the interface circuit 2130 may provide the user with the prediction result generated by the processor 2110. In some embodiments, the interface circuit 2130 may be implemented in a similar manner to that of the interface circuit 1130 of the detection intelligence training device 1100.

The first gas sensing device 2201 may include a controller 2201A, an interface circuit 2201B, sensor arrays 2201C, and a collector 2201D. The second to z-th gas sensing devices 2202 to 220z may be implemented in a similar manner to that of the first gas sensing device 2201, and may operate in a similar manner.

The controller 2201A may control the interface circuit 2201B, the sensor arrays 2201C, and the collector 2201D. For example, the controller 2201A may generate a signal for controlling the interface circuit 2201B, the sensor arrays 2201C, and the collector 2201D by executing programming codes stored in storage (not shown) in the first gas sensing device 2201.

The sensor arrays 2201C may be implemented as arrays including various types of olfactory sensors. In some embodiments, the sensor arrays 2201C may be implemented in a similar manner to that of the sensor arrays 2130 of the mixing gas measuring device 1200, and may operate in a similar manner. The first gas sensing device 2201 may generate multi-modal conditional measurement data by using the sensor arrays 2201C. The generated multi-modal conditional measurement data may be provided to the gas prediction device 2100 through the interface circuit 2201B over the network 2300.

The collector 2201D may collect a gas including a target gas from the surrounding environment of the first gas sensing device 2201. The first gas sensing device 2201 may generate multi-modal conditional measurement data by sensing the collected gas by using the sensor arrays 2201C under a specific condition. For example, the first gas sensing device 2201 may generate multi-modal conditional measurement data through the sensor arrays 2201C under a specific condition in a similar manner to that of the multi-modal sensing unit 2131 of the mixing gas measuring unit 213.

The network 2300 may perform communication between the gas prediction device 2100 and the first to z-th gas sensing devices 2201 to 220z. The first to z-th gas sensing devices 2201 to 220z and the gas prediction device 2100 may exchange data through the network 2300 by wire or wirelessly.

Figure 7:
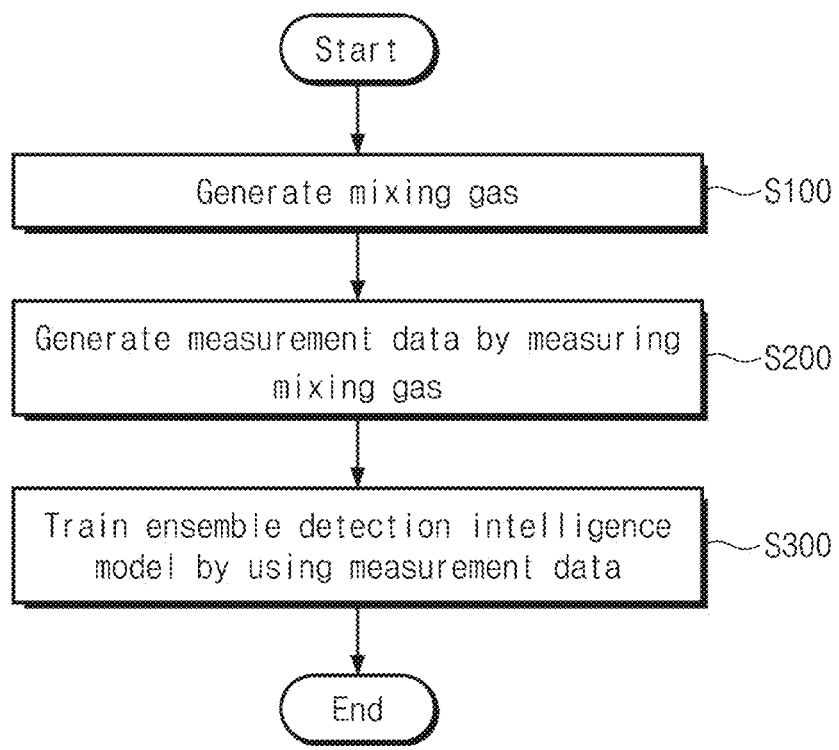
FIG. 7 is a flowchart of an operating method of the detection intelligence training device of FIG. 1.

FIG. 7 is a flowchart of an operating method of the gas detection intelligence training system 10 of FIG. 1. Referring to FIGS. 1 and 7, the gas detection intelligence training system 10 may perform operation S100 to operation S300.

In operation S100, the gas detection intelligence training system 10 may generate a mixing gas. For example, the mixing gas measuring device 1200 of the gas detection intelligence training system 10 may collect and sample the environmental gas GSR, and may sample the target gas GTG. The mixing gas measuring device 1200 may combine sampled environmental gases in various combinations. The mixing gas measuring device 1200 may concentrate the sampled target gas to various concentrations. The mixing gas measuring device 1200 may generate various types of the mixing gases GMX based on the combined environmental gas and the concentrated target gas.

In operation S200, the gas detection intelligence training system 10 may measure the mixing gas. For example, the multi-modal sensing unit 2131 of the mixing gas measuring device 1200 of the gas detection intelligence training system 10 may distribute the mixing gas GMX generated by the mixing gas measuring device 1200 to the sensor arrays 2130. The mixing gas measuring device 1200 may measure the mixing gas GMX by using the sensor arrays 2130 under various sensing conditions. The mixing gas measuring device 1200 may generate the measurement data DGS by synthesizing the measured sensing data for each type of a target gas in time-series.

In operation S300, the gas detection intelligence training system 10 may generate the ensemble detection intelligence model MPDT based on the measured mixing gas. For example, the detection intelligence training device 1100 of the gas detection intelligence training system 10 may generate the detection intelligence training data PDGS by preprocessing the measurement data DGS. The detection intelligence training device 1100 may generate the conditional detection intelligence model MCS by performing multi-modal conditional series deep learning on the detection intelligence training data PDGS. The detection intelligence training device 1100 may generate the ensemble detection intelligence model MPDT by performing domain conversion ensemble deep learning on the detection intelligence training data PDGS and the conditional detection intelligence model MCS.

In some embodiments, the gas detection intelligence training system 10 may combine the gas obtained from the surrounding environment into a plurality of combinations and may adjust the concentration of the detection target gas. The gas detection intelligence training system 10 may mix the combined surrounding environmental gas and the detection target gas, of which the concentration is adjusted, in various ratios. The gas detection intelligence training system 10 may generate a large amount of training data for deep learning from various types of mixing gases. Accordingly, the accuracy of the prediction model trained by the gas detection intelligence training system 10 may be improved.

In some embodiments, the gas detection intelligence training system 10 may operate a sensing device having various modalities under various sensing conditions. The gas detection intelligence training system 10 may sense the detection target gas from the mixed gas at high speed by using the sensing device. Accordingly, the gas detection intelligence training system 10 may generate various types of training data.

In some embodiments, the gas detection intelligence training system 10 may sense a minute amount of target gas through the sensing device without a dedicated single sensor. Accordingly, the convenience and accuracy of the gas detection intelligence training system 10 may be improved.

The above description refers to embodiments for implementing the present disclosure. Embodiments in which a design is changed simply or which are easily changed may be included in the present disclosure as well as an embodiment described above. In addition, technologies that are easily changed and implemented by using the above embodiments may be included in the present disclosure.

While the present disclosure has been described with reference to embodiments thereof, it will be apparent to those of ordinary skill in the art that various changes and modifications may be made thereto without departing from the spirit and scope of the present disclosure as set forth in the following claims.

According to an embodiment of the present disclosure, a gas detection intelligence training system may generate a large amount of samples for generating data required to train a prediction model by mixing a gas of surrounding environments and a target gas in various ratios. The gas detection intelligence training system may generate a large amount of data needed to train the prediction model by measuring a mixing gas with various modalities under various sensing conditions. Accordingly, the accuracy of the gas detection intelligence training system may be improved.

While the present disclosure has been described with reference to embodiments thereof, it will be apparent to those of ordinary skill in the art that various changes and modifications may be made thereto without departing from the spirit and scope of the present disclosure as set forth in the following claims.

What is claimed is:

1. A gas detection intelligence training system, the system comprising:
   a mixing gas measuring device which:
   collects an environmental gas from a surrounding environment;
   generates a mixing gas based on the collected environmental gas and a target gas;
   senses the mixing gas by using a first sensor array and a second sensor array under a first sensing condition and a second sensing condition, respectively; and
   generates measurement data based on the sensed results of the first sensor array and the second sensor array; and
   a detection intelligence training device including a processor which generates an ensemble prediction model based on the measurement data;
   wherein
   the processor generates detection intelligence training data by preprocessing the measurement data;
   generates a first conditional detection intelligence model associated with the first sensing condition and the first sensor array, and
   trains the first conditional detection intelligence model with data associated with the second sensor array among the detection intelligence training data by using transfer learning.

2. The system of claim 1, wherein the mixing gas measuring device:
   generates multi-modal sensing data from the sensed result of the first sensor array and the sensed result of the second sensor array; and
   generates the measurement data from the multi-modal sensing data.

3. The system of claim 2, wherein the processor further:
   generates a second conditional detection intelligence model associated with the first sensing condition and the second sensor array, a third conditional detection intelligence model associated with the second sensing condition and the first sensor array, and a fourth conditional detection intelligence model associated with the second sensing condition and the second sensor array, based on the detection intelligence training data; and generates the ensemble prediction model by training the second to fourth conditional detection intelligence models based on the detection intelligence training data.

4. The system of claim 3, wherein the processor:
samples the measurement data;
processes abnormality data of the measurement data;
processes a missing value of the measurement data; or
normalizes the measurement data.

5. The system of claim 3, wherein the processor:
generates a first time-series series associated with the first sensing condition and the first sensor array from the detection intelligence training data; and
trains the first conditional detection intelligence model based on the first time-series series.

6. The system of claim 3, wherein the processor:
trains the first conditional detection intelligence model and the second conditional detection intelligence model by comparing first data associated with the first sensor array and the first sensing condition with second data associated with the first sensor array and the second sensing condition, from among the detection intelligence training data.

7. The system of claim 3, wherein the processor:
trains the first conditional detection intelligence model and the third conditional detection intelligence model by comparing first data associated with the first sensor array and the first sensing condition with second data associated with the second sensor array and the first sensing condition, from among the detection intelligence training data.

8. The system of claim 3, wherein the processor:
generates a first ensemble training model associated with the first sensor array by combining the first conditional detection intelligence model and the third conditional detection intelligence model based on data associated with the first sensor array among the detection intelligence training data.

9. The system of claim 1, wherein the mixing gas measuring:
classifies the environmental gas into a first environmental gas and a second environmental gas depending on the surrounding environment;
generates a first combination gas by combining the first environmental gas and the second environmental gas; and
generates a first concentration target gas at a first concentration and a second concentration target gas at a second concentration from the target gas.

10. The system of claim 9, wherein the mixing gas measuring device:
generates the mixing gas by combining the first concentration target gas and the first combination gas.

11. The system of claim 10, wherein the mixing gas is a first mixing gas, and
wherein the mixing gas measuring device:
collects a third environmental gas from the surrounding environment;
generates a second combination gas by combining the first environmental gas and the third environmental gas;
generates a third combination gas by combining the second environmental gas and the third environmental gas;

generates a second mixing gas by combining the first concentration target gas and the second combination gas; and
generates a third mixing gas by combining the first concentration target gas and the third combination gas.

12. An operating method of a gas detection intelligence training system, the method comprising:
generating a mixing gas from an environmental gas obtained from a surrounding environment and a target gas;
under a plurality of sensing conditions, sensing the target gas from the mixing gas by using a first sensor array and a second sensor array;
generating detection intelligence training data based on the sensed result;
generating an ensemble detection intelligence model based on the detection intelligence training data; and
training a first domain conversion model set for the first sensor array by using data associated with the first sensor array among the detection intelligence training data and a first intermediate model set for the second sensor array through a transfer learning algorithm.

13. The method of claim 12, wherein the generating of the mixing gas includes:
sampling the environmental gas and the target gas;
combining the sampled environmental gas in a plurality of combination;
concentrating the sampled target gas at a plurality of concentrations; and
mixing the environmental gas, which is combined in the plurality of combinations, with the target gas thus concentrated and sampled, with respect to each of the plurality of concentrations.

14. The method of claim 12, wherein the sensing of the target gas from the mixing gas includes:
distributing the mixing gas to the first sensor array and the second sensor array;
under a first sensing condition among the plurality of sensing conditions, sensing the target gas from the mixing gas during a first time by using the first sensor array;
under the first sensing condition, sensing the target gas from the mixing gas during a second time by using the first sensor array; and
synthesizing the sensed results under the first sensing condition.

15. The method of claim 12, wherein the generating of the ensemble detection intelligence model includes:
training a first intermediate model set for a time point, at which the target gas is sensed from the mixing gas, by using the detection intelligence training data;
training a second intermediate model set for a relationship between the first sensor array and the plurality of sensing conditions, by using the detection intelligence training data and the first intermediate model set; and
training a conditional detection intelligence model by using the detection intelligence training data and the second intermediate model set, by comparing the first sensor array with the second sensor array.

16. The method of claim 12, further comprising:
combining models included in the first domain conversion model set by using the data associated with the first sensor array among the detection intelligence training data.

* * * * *